United States Patent
Persoon et al.

(10) Patent No.: US 8,754,384 B1
(45) Date of Patent: Jun. 17, 2014

(54) SAMPLE PREPARATION STAGE (71) Applicant: FEI Corporation, Hillsboro, OR (US)

(72) Inventors: Johannes A. H. W. G. Persoon, Waalre (NL); Andreas Theodorus Engelen, Eindhoven (NL); Mathijs Petrus Wilhelmus van den Boogaard, Boxtel (NL); Rudolf Johannes Peter Gerardus Schampers, Tegelen (NL); Michael Frederick Hayles, Eindhoven (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/158,633

(22) Filed: Jan. 17, 2014

Related U.S. Application Data (60) Provisional application No. 61/762,457, filed on Feb. 8, 2013.

(30) Foreign Application Priority Data

Feb. 8, 2013 (EP) ..................................... 13154537

(51) Int. Cl.
- *G01F 23/00* (2006.01)
- *G01N 23/00* (2006.01)
- *G21K 7/00* (2006.01)

(52) U.S. Cl.
USPC ....... 250/440.11; 250/306; 250/309; 356/616

(58) Field of Classification Search
USPC ............ 250/306, 307, 309–310, 311, 440.11, 250/442.11, 492.1, 492.2, 492.3, 492.21; 356/614, 615, 616
See application file for complete search history.

(56) References Cited

U.S. PATENT DOCUMENTS

| | | | |
|---|---|---|---|
| 2,656,718 A * | 10/1953 | Dames et al. | .............. 73/791 |
| 5,435,850 A | 7/1995 | Rasmussen | |
| 5,986,270 A | 11/1999 | Bormans et al. | |
| 6,758,362 B2 | 7/2004 | Studer | |
| 6,963,068 B2 * | 11/2005 | Asselbergs et al. | ........... 250/311 |
| 7,034,316 B2 | 4/2006 | Wagner et al. | |
| 7,413,872 B2 | 8/2008 | Frederik et al. | |
| 7,474,419 B2 | 1/2009 | Tappel et al. | |

(Continued)

FOREIGN PATENT DOCUMENTS

| | | |
|---|---|---|
| EP | 2 009 422 | 12/2008 |
| WO | WO 2012/038484 | 3/2012 |
| WO | WO 2012/155044 | 11/2012 |

OTHER PUBLICATIONS

Extended European Search Report issued Feb. 7, 2013 in EP Application No. 13154537.8.

(Continued)

*Primary Examiner* — Bernard E Souw (74) *Attorney, Agent, or Firm* — Knobbe, Martens, Olson & Bear LLP

(57) ABSTRACT

Described is a system and method for in situ sample preparation and imaging. The system includes a multi-axis stage 100 having a bulk stage 110 and a grid stage 150 with various degrees of freedom to allow for sample preparation. In some embodiments, a focused ion beam system is used to prepare a lamella on the bulk stage 110. The lamella can then be transferred to the grid stage 150 from the bulk stage 110 without needing to move the multi-axis stage 100 from the focused ion beam system.

18 Claims, 5 Drawing Sheets

(56) References Cited

U.S. PATENT DOCUMENTS

| | | |
|---|---|---|
| 7,675,049 B2 | 3/2010 | Schmidt et al. |
| 7,884,326 B2 * | 2/2011 | van de Water et al. ....... 250/311 |
| 8,011,259 B2 | 9/2011 | Dona |
| 8,374,802 B2 * | 2/2013 | Treptow et al. ................ 702/32 |
| 2007/0063148 A1 | 3/2007 | Miyazaki et al. |
| 2008/0296498 A1 * | 12/2008 | Hong ............................ 250/311 |
| 2012/0003394 A1 | 1/2012 | Mulders et al. |
| 2012/0074320 A1 | 3/2012 | Biberger et al. |

OTHER PUBLICATIONS

Stokes, et al. "Methodologies for the preparation of soft materials using CryoFIB SEM", Proc. of SPIE vol. 7378 73780G-12.

* cited by examiner

SAMPLE PREPARATION STAGE

INCORPORATION BY REFERENCE TO ANY PRIORITY APPLICATIONS

This application claim priority to U.S. Provisional Application 61/762,457 filed Feb. 8, 2013 and EP Provisional Application No. 13154537.8 filed Feb. 8, 2013, the entirety of which are hereby incorporated by reference. Any and all applications for which a foreign or domestic priority claim is identified in the Application Data Sheet as filed with the present application are hereby incorporated by reference under 37 CFR 1.57.

BACKGROUND OF THE INVENTION

1. Field of the Invention

The present embodiments relate to devices and methods of sample preparation for imaging systems. More specifically, the present embodiments relate to a sample preparation stage having multiple degrees of freedom allowing for in situ sample preparation and imaging.

2. Description of the Related Art

Samples for electron microscope imaging require certain preparation for observation under transmitted light or electron radiation. For example, thin slices (or sections) of a sample are typically cut or milled from a bulk sample in a grid or tube. The cutting or milling can be performed by a focused ion beam (FIB) system, or within a dual beam system that includes both a FIB and an electron microscope. Examples of such dual beam systems include the Quanta 3D DualBeam systems from FEI Corporation (Hillsboro, Oreg., USA). However, after the thin slices are prepared using the FIB, the samples must then be transferred to a platform suitable for imaging. Microscopic imaging, such as scanning transmission electron microscope (STEM), can require positioning along multiple degrees of freedom in order to capture a proper image.

Others have prepared stages for STEM imaging that have multiple degrees of freedom. For example, U.S. Pat. No. 7,474,419 describes a stage assembly for positioning a sample in the vicinity of a reference point. The stage assembly includes a sample table to which the sample can be mounted and a set of actuators arranged so as to effect translation of the sample table along directions substantially parallel to an X-axis perpendicular to a reference plane, a Y-axis parallel to the reference plane, and a Z-axis parallel to the reference plane. The X-axis, Y-axis and Z-axis are mutually orthogonal and passing through the reference point. In addition, U.S. Pat. No. 6,963,068 describes a manipulator that has a table that can be moved in five degrees of freedom, with three perpendicular translations and two rotations.

However, techniques for manipulating samples for STEM or TEM analysis are more complex, and can require manipulating samples for both FIB milling and carving and the later STEM analysis to be performed at specific, critical temperature to prevent ice crystal formation in the sample, or undesirable thawing of the sample between manipulations. Thus, what is needed is a system that allows for complex manipulations of samples for STEM or TEM imaging without the requiring so much sample handling that the sample becomes destroyed.

SUMMARY OF THE INVENTION

One embodiment is a multi-axis sample preparation stage, that includes a bulk sample holder configured to rotate a sample position about a first bulk axis parallel to the direction of the bulk sample holder and also rotate the sample position about a bulk flip axis that is perpendicular to the direction of the bulk sample holder; and a grid sample holder for holding a sample grid adjacent the bulk sample holder and configured to rotate the sample grid about a first grid axis parallel to the direction of the grid sample holder and a grid flip axis that is perpendicular to the direction of the grid sample holder.

Another embodiment is a dual beam system having a focused ion beam and a scanning electron microscope. This system includes a multi-axis sample preparation stage having a bulk sample holder configured to rotate about a first bulk axis parallel to the direction of the bulk sample holder and also rotate about a bulk flip axis that is perpendicular to the direction of the bulk sample holder; and a grid sample holder adjacent the bulk sample holder and configured to rotate about a first grid axis parallel to the direction of the grid sample holder and a grid flip axis that is perpendicular to the direction of the grid sample holder.

Still another embodiment is an in situ method of preparing a sample by providing the multi-axis sample preparation stage as described above, and then cutting a lamella from a sample stored in the bulk sample holder; and transferring the lamella from the bulk sample holder to a grid on the grid sample holder.

DETAILED DESCRIPTION

Embodiments of the invention relate to sample processing systems and methods for preparing a sample for imaging in an electron microscope. One embodiment of the invention is a sample preparation and imaging stage for a dual beam electron microscope that has multiple sample locations and the ability to tilt each sample location about several axes. One embodiment of the multi-axis stage has a bulk preparation stage for manipulating a bulk sample, for example by performing a focused ion beam treatment of the bulk sample to mill or slice off a lamella of the sample for further imaging. The multi-axis stage can include a holder for a grid, tube, planchet or TEM liftout grid in order to handle a variety of sample types. In addition, the multi-axis stage may be configured to move in multiple directions with multiple degrees of freedom so that the bulk sample can be positioned under a FIB to properly mill or slice the bulk sample.

In addition to the bulk preparation stage, embodiments of the multi-axis stage also include a grid stage which is configured to hold a thin structure (e.g., lamella) of the bulk sample mounted onto a grid for imaging. Thus, once cut, a lamella from the bulk sample can be transferred from the bulk stage to the grid stage by using a manipulator needle. In some embodiments, because the grid stage can move in multiple dimensions, it is possible to perform dual axis tomography where more than one angle can be viewed. Because the bulk stage and grid stage are on the same multi-axis stage, a single multi-axis stage can be used to cut a lamella and also then perform TEM scanning on the cut lamella section without venting a chamber used to transfer the lamella to the grid stage. The multi-axis stage can thus include a bulk stage with multiple degrees of freedom and a grid stage with multiple degrees of freedom along various axes which allows the components of the system to move in multiple dimensions with respect to one another.

It should be realized that many different types of treatments can be applied to a sample, as discussed below. Embodiments of the invention include any type of treatment that may be used for preparing a sample for transmission electron microscope (TEM) or scanning transmission electron microscope (STEM) analysis. For example, a lamella may be prepared from a site located in a bulk sample. In this system, the bulk stage would hold a bulk sample in which a lamella site would be located. The lamella would then be prepared on the bulk stage.

In addition, it should be realized that the present embodiments are not limited to any particular configuration of microscope. For example, any type of microscope that is used to capture images of a sample is within the scope of the present embodiments. Such microscopes include, for example, visible light microscopes, confocal microscopes, and infrared and near infrared microscopes. Those skilled in the art will recognize that embodiments exemplified herein with regard to an electron microscope can be readily adapted to other types of microscopes.

In another embodiment, a lift out procedure may be performed. In this system, a manipulator may transfer a lamella located on the bulk stage to a grid on a grid stage. In some embodiments, the lamella may be further processed after the manipulator is removed. For example, the lamella may be milled from a thick lamella to a thin lamella using a focused ion beam.

Lamella preparation can include processes such as locating a lamella site (including multiple cross sections of the sample), protective deposition (e.g., coating the lamella site with a metal cap layer), adding fiducial markers, rough milling (e.g., to create lamella about 2 µm), medium milling (e.g., to thin lamella to about 250-400 nm), fine milling (e.g., to thin the lamella to a final thickness), undercutting to release sample from the substrate, endpointing, cleaning lamella (e.g., low kV cleaning), and/or transferring the sample.

With focused ion beam systems, the lamella can be positioned accurately within the instrument's mean drift (including, for example, both sample drift, due to imaging or charging, and stage drift). In addition, in some embodiments, fiducial markers can be used to improve location of a particular feature during cross-sectioning. During final thinning, the user can thin the lamella until the precut (and filled) fiducial markers are seen in a cross-section image. In some embodiments, the fiducial markers (for example, lines) can be milled at about 100 nm width, which can form a basis for judging the final thickness of the lamella.

To form the fiducial markers, small beams (for example, less than about 100 pA) and relatively short dwell times can be used. These fiducial markers can be conveniently scripted. With dual-beam systems, the SEM or S/TEM (scanning transmission electron microscope) can be used to improve the registration by stopping the thinning at a particular image location. Without a dual beam for final location, the measured accuracy is on the order of 50 nm (3 sigma) for top-down FIB-prepared systems. Refinement in a small dual beam can allow a practiced operator nm-level placement. To measure placement accuracy, there are a few different metrics: the placement of the fiducial marker relative to the feature, as well as the placement of the final lamella as compared to the initial fiducial marker. Overall placement can also be judged by measuring the final placement of a known reference feature within a lamella.

In some embodiments, focused ion beam methods can be used for one or more lamella preparation processes. For example, FIB techniques can be used for site-specific analysis, deposition, and ablation of materials. It will be appreciated that while an SEM uses a focused beam of electrons to image the sample in the chamber, an FIB setup uses a focused beam of ions that can be operated at low beam currents for imaging or high beam currents for site specific sputtering or milling. FIB can also be incorporated in a system with both electron and ion beam columns, allowing the same feature to be investigated using either of the beams.

In some embodiments, the location of the lamella can be positioned to find an isolated feature, or to fully encapsulate a reference feature in the bulk sample. For example, where only a single feature is needed, the lamella can be prepared at a slight angle to the feature. As described herein, the bulk stage may be rotated about an axis and/or flipped about an axis such that the bulk sample is rotated or flipped for positioning the lamella location.

Current FIB systems have high resolution imaging capability; this capability coupled with in situ sectioning has eliminated the need, in many cases, to examine FIB sectioned specimens in a separate SEM instrument. SEM imaging is still required for the highest resolution imaging and to prevent damage to sensitive samples. However, the combination of SEM and FIB columns onto the same chamber enables the benefits of both to be utilized.

FIB can also be used to deposit material via ion beam induced deposition. For example, FIB-assisted chemical vapor deposition occurs when a gas, is introduced to a vacuum chamber and allowed to chemisorb onto the sample. By scanning an area with the beam, the precursor gas will be decomposed into volatile and non-volatile components; the non-volatile component, such as tungsten, remains on the surface as a deposition. This is useful, as the deposited metal can be used as a sacrificial layer, to protect the underlying sample from the destructive sputtering of the beam. From nanometers to hundreds of micrometers in length, metal deposition allows for metal lines to be deposited where needed. Materials such as tungsten, platinum, cobalt, carbon, gold, and the like, can be deposited.

A fiducial marker or fiducial can be an object placed in the field of view of an imaging system which appears in the image produced, for use as a point of reference or a measure. A fiducial marker may be something placed into or on the sample. In some embodiments, preparation of the sample can include surface and/or buried fiducials (e.g., fixed reference points). An effective fiducial creation strategy can have a large impact on the robustness of an automated process. For example, different fiducial marker shapes can have very different behaviors.

Transmission electron microscope (TEM) requires very thin samples, nowadays typically between 50 to 300 nm. The nanometer-scale resolution of FIB allows an exact thin region to be selected and prepared. In some embodiments, lower beam voltages, or further milling with a low-voltage argon ion beam after completion of the FIB process can reduce surface damage and implantation, which produce noticeable effects when using techniques such as high-resolution "lattice imaging" TEM or electron energy loss spectroscopy.

In some embodiments, rough, medium, and/or fine milling can be used to adjust the size or thickness of the lamella. Decreasing FIB beam sizes can be used to improve control of the rough, medium, and/or fine milling. It will be appreciated that there is a tradeoff between slow etch time (which can cause increased drift sensitivity) and beam resolution. In some embodiments, the procedure uses 13 nA for bulk milling and undercutting, 1 nA for medium thinning, 30-100 pA for fine milling, and 3 kV-120 pA (using 1000 pA aperture) for final cleaning. However, variations such as 3 nA instead of 1 nA for medium thinning are possible, depending on user preference and the details of the available aperture strip.

In transmission techniques, analysis is greatly simplified for single scattering events. In addition, the sample attenuates the beam, the attenuation a function of sample material (high-Z materials showing a higher attenuation than low-Z materials) and sample thickness. Generally, S/TEM samples have a thickness of about 80 nm. For TEM, samples generally have a thickness range from about 20 nm to about 80 nm, depending on the specific sample and TEM tool. Thickness can be measured either by cross-sectioning the thin lamella, or by measuring the electron beam attenuation. At low electron beam energies (e.g., 30 keV) thin samples can be used. At high electron beam energies (e.g., 300 keV) thicker samples can be used, for example biological material of up to about 1 μm or semiconductor materials of typically less than 100 nm may be used.

In some embodiments, top-down measurement of TEM sample thickness can be influenced by the deposited protective overcoat. In some embodiments, cross-section measurements of the lamella are much more accurate and useful. In some embodiments, lamella thickness is substantially uniform. In other embodiments, samples are intentionally made with varying thickness. For example, in some embodiments, the shape of the lamella is a wedge.

The process can also be simplified using the systems and methods as described herein, by setting up the system at the FIB's eucentric point. For example, tilt stage systems (e.g., the bulk stage and/or the grid stage) have an option to set the eucentric point based on the coincident point, the FIB's eucentric, or the SEM's eucentric. By setting the tool according to the FIB's eucentric point beam shift and motion during sample preparation can be avoided. It will be appreciated that the microscope can be tuned by setting beam tilt pivot points to the right level, for example, by eucentricity, precise focus, pivot point adjustment, and accurate rotation center.

Sample (e.g., lamella) transfer mechanisms fall into two general types: the in situ autoprobe, and ex situ plucking with a glass rod. Each method has benefits, depending on the application target. For example, ex situ liftout is typically significantly faster.

Endpointing in sample preparation generally uses a SEM signal to look at either secondary or backscattered electrons from a sample, and correlates these to thickness. In some embodiments, the method uses the brightness. For example, very thin samples become either dark or bright (depending on detector layout and source) once thinned under about 100 nm. It will be appreciated that the exact value depends on the beam energy and imaging mode. Similar techniques can be used with the integrated S/TEM detector system, with the added advantage of enhanced resolution over SEM-based techniques. The S/TEM system allows direct thickness measurements to be made from first principles, or contrast differential techniques can be used in darkfield microscopy.

The system and methods disclosed herein can be used for sample preparation of cryogenically frozen samples. For example, the methods can be performed without venting the microscope chamber. FIB preparation can be used with cryogenically frozen samples in a suitably equipped instrument such as a dual beam microscope, allowing cross sectional analysis of samples containing liquids or fats, such as biological samples, pharmaceuticals, foams, inks, and food products. As discussed in more detail below, the system can further include temperature control elements for maintaining a temperature in the system. Accordingly, in some embodiments, the methods disclosed herein can be performed at room temperature, elevated temperatures, and/or at cryogenic temperatures.

As used herein, the term "sample" can include any type of sample from a biological organism, but typically includes tissue, cells, viruses, cell structures, or any other biological sample of interest.

The sample can be prepared for electron microscopy to be used in material science applications, such as for semiconductor materials or polymers. Electron microscopy may also be used in the biological and life sciences fields for applications such as diagnostic electron microscopy, cryobiology, protein localization, electron tomography, cellular tomography, cryo-electron microscopy, toxicology, biological production and viral load monitoring, particle analysis, pharmaceutical quality control, structural biology, 3D tissue imaging, virology, and vitrification. These separate types of applications can be performed by a range of different types of electron microscopes including, for example, transmission electron microscopes (TEM), scanning electron microscopes (SEM), reflection electron microscopes, scanning transmission electron microscopes, and low-voltage electron microscopes.

Overview of Sample Preparation System

Figure 1:
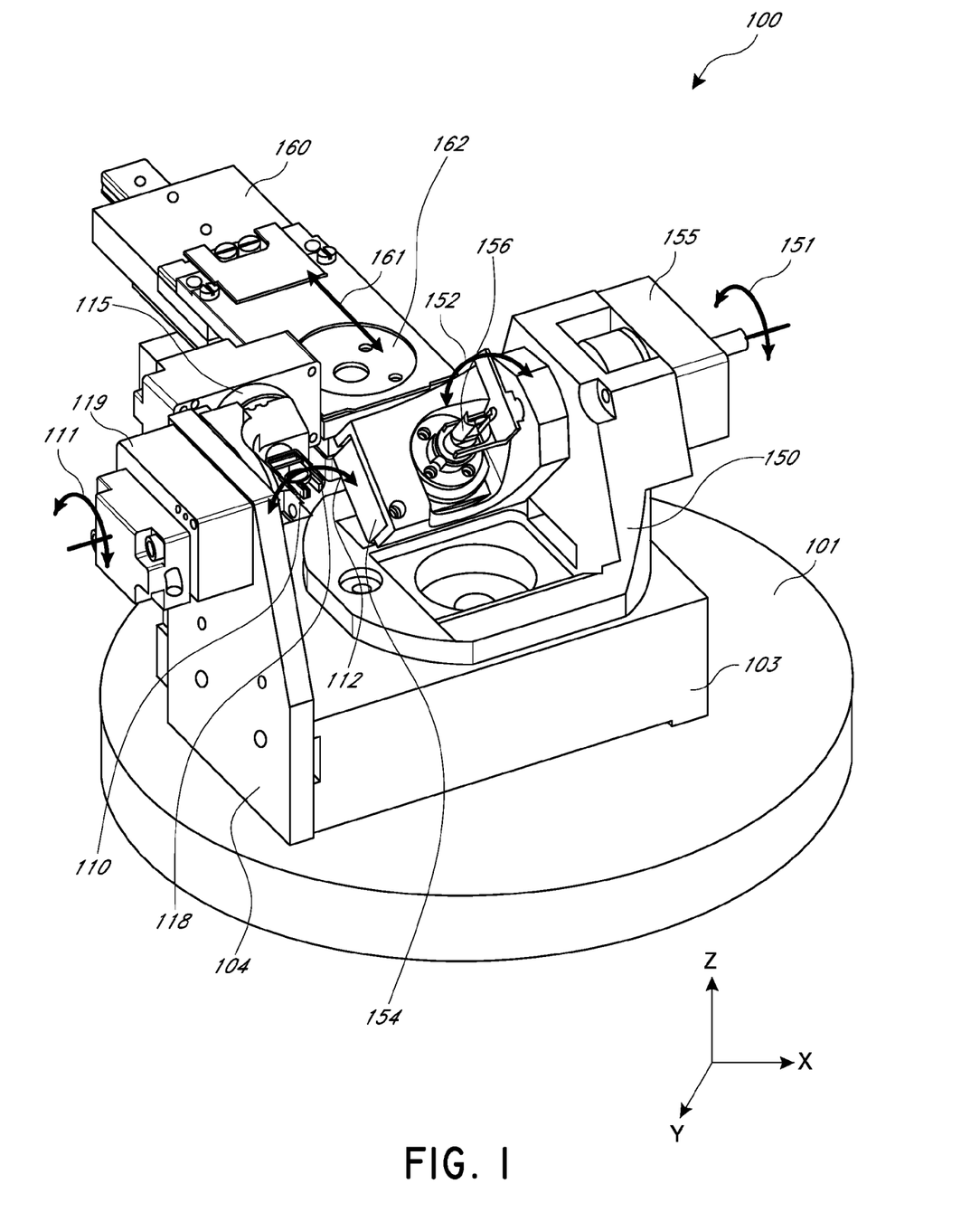
FIG. 1 is a perspective view of one embodiment of a base stage having a bulk stage and a grid stage.

FIG. 1 is a perspective view of one embodiment of a multi-axis stage 100. The multi-axis stage 100 includes a circular base 101 that is supporting a rectangular stand 103. Mounted on a left edge of the rectangular stand 103 is vertical wall 104 that holds a bulk stage 110. The bulk stage 110 is movably mounted to the vertical wall 104 and used to hold a bulk sample.

The bulk stage 110 includes a bulk rotation actuator 115 configured to rotate a sample holder 118 circumferentially about a bulk rotation axis 112 as illustrated. Thus, movement of the actuator 115 results in rotational movement of the bulk sample in the sample holder 118 with 360 degrees of movement around the Y axis of the multi-axis stage 100. This allows the sample to be rotated along an axis that is parallel to the direction of the sample holder 118.

In addition to this rotational movement, the bulk stage 110 also has multiple degrees of freedom about a bulk flip axis 111 which uses a flip actuator 119 mounted to the vertical wall 104 to rotate the sample holder 118 around the X axis to "flip" the sample from the front of the base stage 100 to the rear of the multi-axis stage 100 and back. This allows the bulk sample holder 118 to rotate around a line that is perpendicular to the direction of the sample holder.

Rotation of a bulk sample about the bulk rotation axis 112 allows a sample treatment, such as a focused ion beam treatment, to result in a rotationally symmetric sample about the rotation axis. This can remove, or reduce, non-isotropy/inhomogeneity in the sample after ion beam treatment. Together with this angular degree of freedom (DOF) about the rotation axis, the further angular DOF provided about the bulk flip axis 111 allows a wide range of specific crystallographic orientations in the sample to be oriented along the first and/or second irradiating beam. Thus, the combined angular DOFs about the rotation axis and the flip axis allow both α-tilt and β-tilt of the sample.

In a particular embodiment, the angular stroke of the sample holder 118 about the bulk flip axis is substantially 360 degrees or more. If the flip axis is arranged to be parallel to a principal axis (by suitable angular adjustment of the stage assembly about the rotation axis) of the multi-axis stage 100, and the focused beam is an ion beam, such an angular stroke allows the stage assembly to be used as a type of "ion lathe". In such a set-up, one could manufacture various precision items, such as tips and probes that are required to have a particular cylindrical/conical profile about the flip axis. In a similar fashion, one could realize a "laser lathe", using a laser beam as the second irradiating beam.

Mounted to the rectangular stand 103 and directly adjacent the bulk stage 110 is a grid stage 150. Similar to the bulk stage, the grid stage 110 is mounted to the rectangular stand 103 so that is also provides a sample with multiple degrees of freedom about several axes. As indicated in FIG. 1, the grid stage 110 has a grid flip axis 151 and a grid rotation axis 152 that allow movement of a grid holder 156 in multiple X and Y dimensions. Rotational movement along the grid rotation axis 152 is controlled by a grid rotation actuator 154 and moves the grid holder 156 around the Y axis of the multi-axis stage 100. The allows the grid holder to rotate in a direction that is parallel to the grid holder 156.

Rotational movement along the grid flip axis 151 is controlled by a flip actuator 155 which allows the grid holder to rotate about the X axis of the multi-axis stage 100. This allows the grid stage to rotate in a direction around the Y axis of the multi-axis stage 100. This multi-axis rotational movement provides several degrees of freedom for samples placed into the grid holder 156 to provide imaging of the sample.

As can be realized, by having the bulk stage and the grid stage located adjacent one another and mounted to the same base, one can use this single stage for preparing samples using an ion beam, and then imaging those samples with an electron beam. In a dual beam device, the multi-axis stage can be placed within the device and then used to prepare and image samples without the requirement of removing the multi-axis stage from the dual beam device. Moreover, as discussed below, samples can be kept at a desired temperature by cooling or heating the multi-axis stage to a desired temperature and then performing all of the sample manipulations within a dual beam system without needing to expose the stage and samples to room temperature conditions.

At the rear portion of the multi-axis stage 100 is a STEM stage 160 that allows transverse movement 161 of a detector holder 162 for performing a scanning transmission electron microscopy on a sample using the same multi-axis stage 100. In some embodiments, the aforementioned components can move about the axes independent of one another.

At the rear portion of the multi-axis stage 100 a retractable S/TEM detector can be placed at in the detector holder 162 that can be retracted by retractor 160. The detector can also be protected by a cover to avoid, for example, radiation damage or chemical damage. In some embodiments the cover may be used in place of the retractability of the S/TEM detector.

Figure 2:
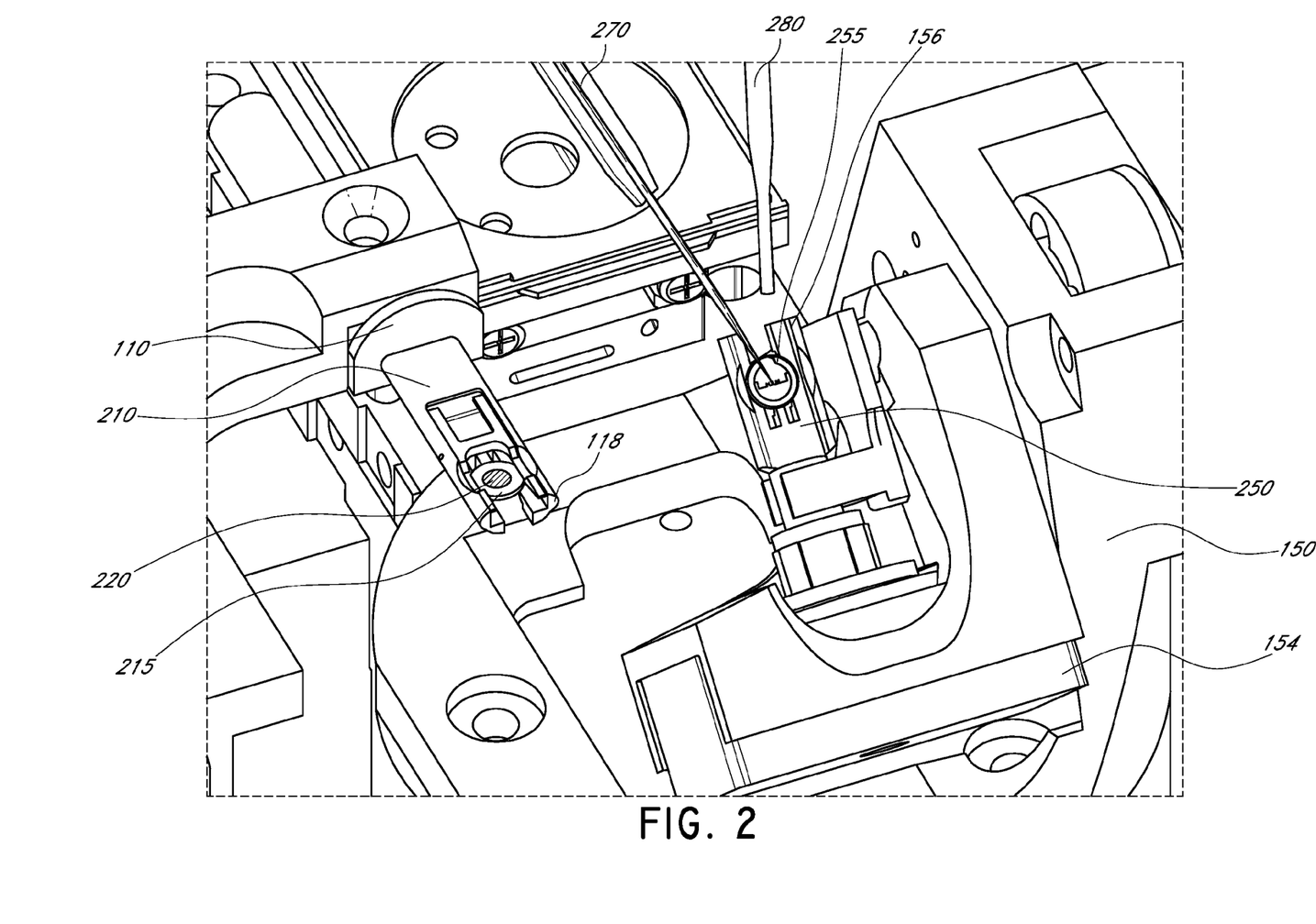
FIG. 2 is an enlarged view of the bulk stage and the grid stage of FIG. 1A.

FIG. 2 is an enlarged view of one embodiment of the bulk stage 110 and the grid stage 150 showing their relationship to one another. The bulk stage includes a bulk arm 210 configured to hold a bulk sample carrier 215 with a bulk sample 220. The bulk arm 210 can rotate about the bulk stage such that the orientation of the bulk sample 220 changes. For example, the bulk arm 210 can rotate about the bulk rotation axis 112 to rotate the bulk sample 220. The bulk arm 210 can also flip about the bulk flip axis 111 to flip the bulk sample 220.

Adjacent the bulk stage 110 is the grid stage 150 which is shown with a grid arm 250 configured to hold a grid plate 255 that is configured to hold a sample. The grid arm 250 can move about the grid stage with multiple degrees of freedom such that the orientation of the grid plate 255 changes over time and during electron microscopy. For example, the grid arm 250 can rotate about the grid rotation axis 152. The grid arm 250 can also flip about the grid flip axis 152 to flip the grid plate.

Figure 3:
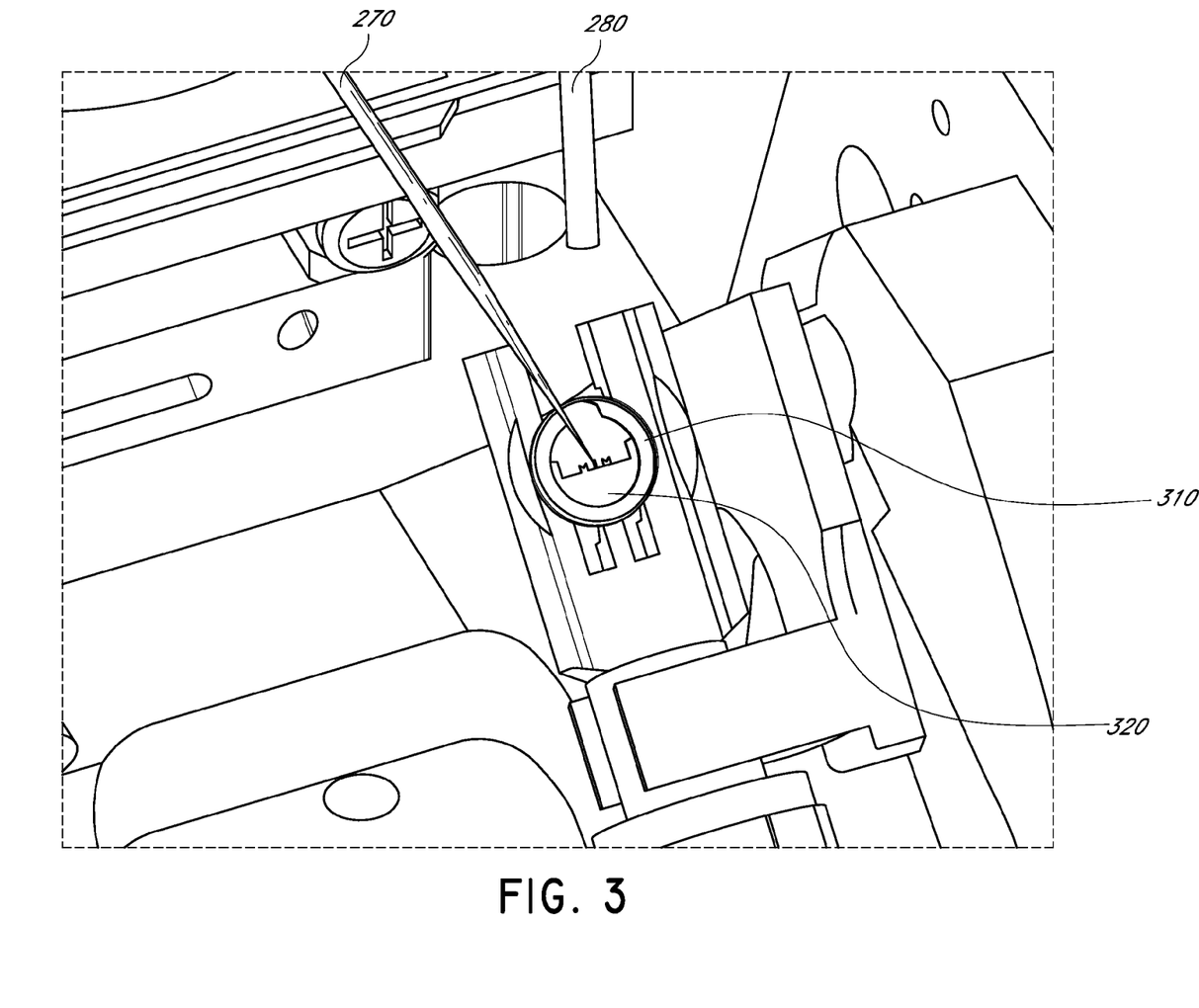
FIG. 3 is an enlarged view of the prepared sample of FIG. 3.

As shown in FIG. 2, a manipulator 270 and a gas supply system 280 can be used transfer a lamella taken from the sample 220 at the bulk stage 110 and move the lamella to the grid stage 150 by methods known in the art. As shown in FIG. 3, the lamella 410 can be mounted to the grid plate 255 for further analysis.

Of course, it should be realized that the present embodiments are not limited to any particular configuration of bulk sample carrier 215. For example, any type of sample carrier that used to hold a sample and allow for preparation as disclosed herein, is within the scope of the present embodiments. Similarly, it should be realized that the present embodiments are not limited to any particular configuration of the grid plate 255. For example, any type of plate that used to hold a sample and allow for further processing and/or imaging as disclosed herein, is within the scope of the present embodiments.

Exemplary Methods for Sample Preparation

Figure 4:
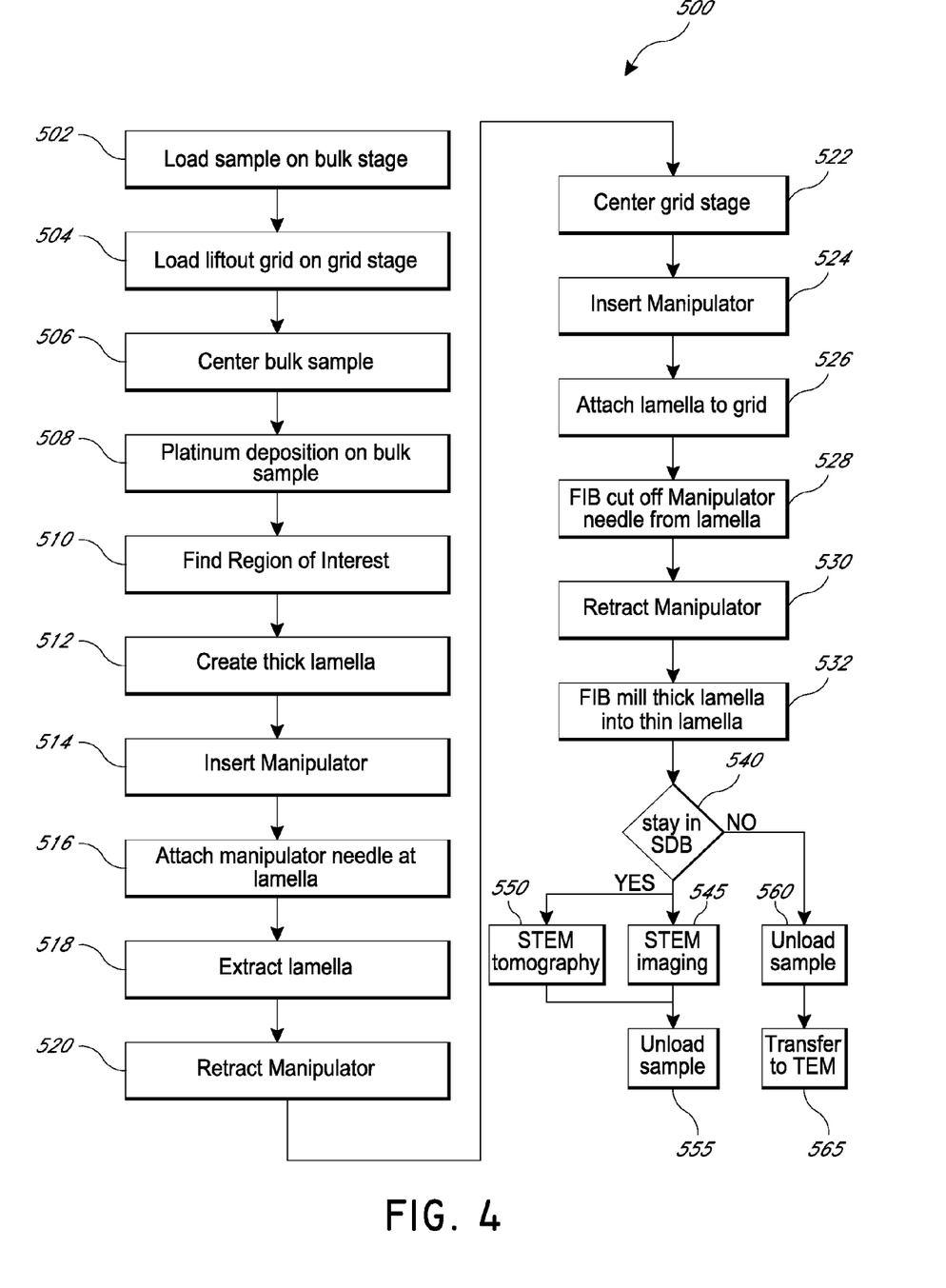
FIG. 4 is a flow diagram of one embodiment of a method for in situ preparation of a sample for imaging.

FIG. 4 shows a flowchart illustrating an exemplary process 500 that may run within one implementation of a sample preparation system 100. Process 500 begins at block 502, where the bulk sample is loaded on the bulk stage. After the bulk sample has been loaded onto the bulk stage, the process moves to block 504, wherein a liftout grid is loaded on the grid stage. Process 500 then moves to block 506, where the bulk sample is centered on the bulk stage. For example, the bulk sample can be positioned by rotating the bulk sample arm about the bulk rotation axis and/or flipping the bulk sample arm about the bulk flip axis to properly position the bulk sample for creating a desired lamella.

Once the bulk sample has been positioned, the process 500 moves to block 508, where a protective metal layer is locally deposited on the bulk sample. It should be realized that in other embodiments, the order to blocks 508 and 510 can be reversed. As discussed herein, the protective metal layer can include any material, such as, for example, platinum or tungsten. Process 500 then moves to block 510, where a region of interest on the bulk sample is determined by the user. The region of interest can include, for example, one or more isolated features and/or one or more reference features, such as a fiducial marker in the deposited protective metal layer. Alternatively, the region of interest can be marked by having previously placed the sample in an optical microscope and using a laser marker to indicate the region of interest.

Once a region of interest has been located, process 500 moves to block 512, where a lamella is cut. As discussed herein, the lamella may be positioned to optimize the feature of interest location. In some embodiments, a thick lamella is cut. In one embodiment, the lamella is cut using a focusing ion beam that is targeted to cut a desired lamella from the bulk sample. As can be appreciated, the desired region is properly cut by using the multiple degrees of freedom provided by the bulk stage, as described above. Once the lamella has been cut, the lamella is transferred from the bulk stage to the grid stage by an operator. As one example, at block 514 a manipulator is inserted into the bulk sample and at block 516 the manipulator is then attached to the lamella that has been cut from the bulk sample. The manipulator can be, for example, a needle or other device configured to attach to a lamella. For example, the manipulator may be temporarily attached to the lamella to enable transport between the bulk stage and the adjacent grid stage. The manipulator then extracts the lamella at block 518. And the manipulator is retracted from the bulk sample at block 520.

Process 500 then moves to block 522, where the liftout grid on the grid stage is centered. For example, the liftout grid can be positioned by rotating the grid arm about the grid rotation axis and/or flipping the grid arm about the grid flip axis. The manipulator with the lamella is then inserted at block 524 and the lamella is attached to the liftout grid at block 526. Once the lamella is attached to the liftout grid, the process 500 moves to block 528, wherein the manipulator is detached from the lamella. For example, a FIB can be used to cut the manipulator needle from the lamella. The manipulator can then be retracted at block 530.

As discussed herein, in some embodiments, the lamella can be thinned from a thick lamella to a thin lamella. For example, the process 500 moves to block 532, where the thick lamella is thinned to a thin lamella by a focused ion beam.

After the lamella has been transferred to the grid stage and thinned to the desired thickness, process 500 moves to decision block 540 to determine if the lamella will be examined in a small dual beam device (SDB). If a decision is made to not stay within the SDB device, then multi-axis stage 100 can be unloaded at block 560 and transferred to, for example, a TEM system at block 565. However, if a decision is made to remain with the SDB device, the sample can be directly STEM imaged. For example, the sample can undergo STEM tomography at block 550 before being unloaded at block 555. In another example, the sample can undergo STEM imaging at block 545 before being unloaded at block 555.

It is noted that embodiments of the invention also cover variants of the method, in which, for example, step 502 and 504 are exchanged, or blocks 510 and 508, etc., as is clear to the person skilled in the art.

Temperature Control of Multi-Axis Stage

Figure 5:
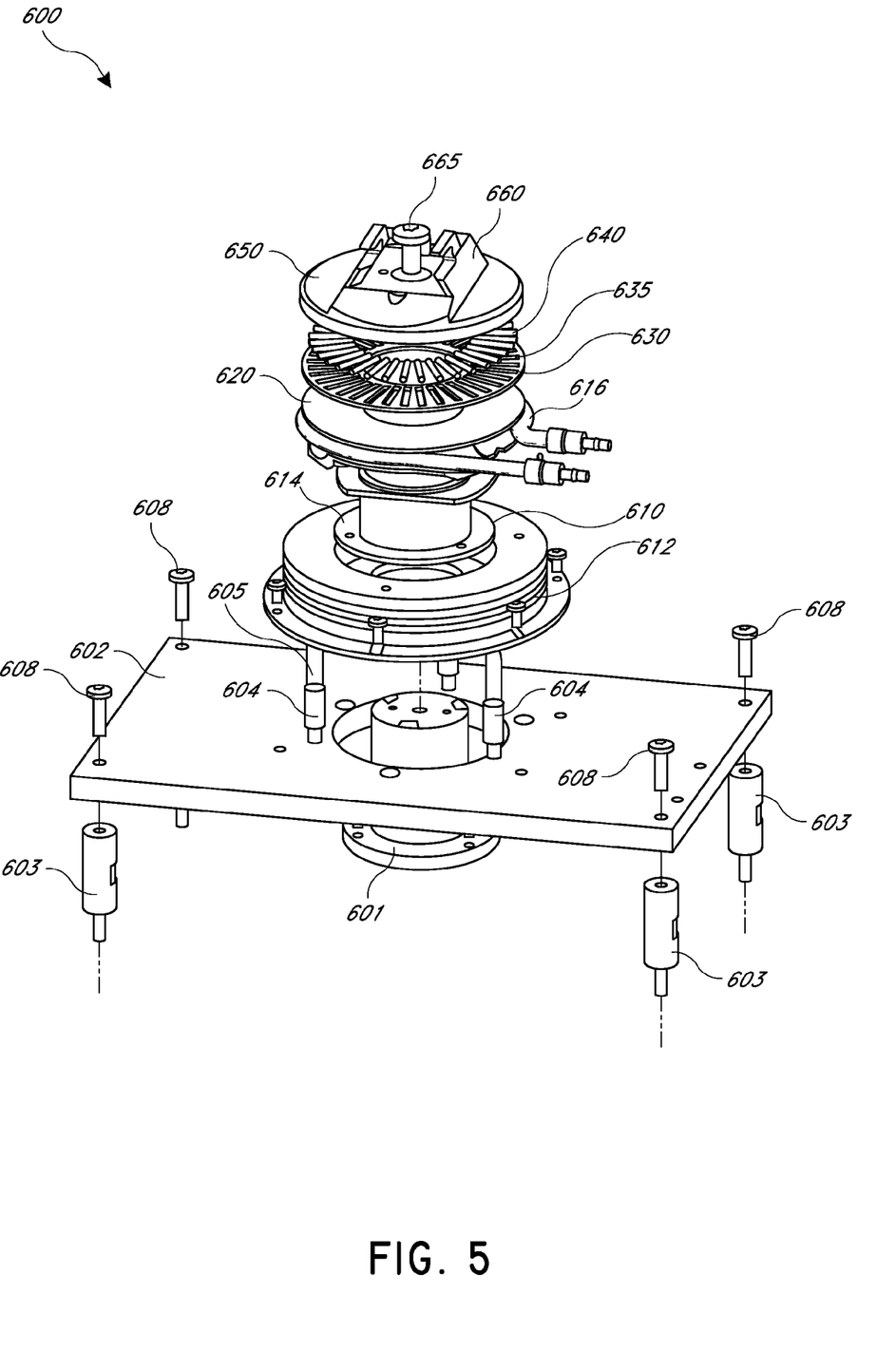
FIG. 5 is a perspective view of one embodiment of a heating/cooling element via bearings.

In some embodiments, the system can further include a thermal control system configured to control the temperature of the multi-axis stage 100 As shown in FIG. 5, a thermal control system 600 can be used to heat or cool the multi-axis stage 100 but still allow the stage 100 to move circularly within an imaging system. The thermal control system 600 includes a base 601 that mounts through a platform 602 via a series of connectors 604. A system of standoffs 603 may be used to raise the platform 602 to a desired level within the imaging system. The standoffs are mounted to the platform 602 through a series of pins 608.

As shown, the base 601 fits within a cylindrical sleeve 610 that mates into the center of a metal ring 612. Mated to a top surface 614 of the sleeve 610 is a heat transfer body 620 including a heat transfer pipe 616 that is configured to move a heat transfer medium. In one embodiment, the heat transfer medium is cooled dry or liquid nitrogen and the temperature of the heat transfer plate 620 can be controlled by controlling the flow rate of the dry nitrogen with a flow meter (not shown) or adding a supplemental heat source, such as a thermal resistor. Thus, by controlling the type and amount of heat transfer medium circulating through the head transfer pipe 616 (and/or controlling the extra heat source), the user can control the resulting temperature of the heat transfer plate 620.

Above and in thermal contact with the heat transfer plate 620 is a bearing ring 630 that has a plurality of slots 635. Each of the slots 635 in the bearing ring 630 are configured to hold thermally conductive rollers 640. Above the rollers 640 is a top plate 650. The top plate 650 includes a mounting bracket 660 and centering pin 665 that are designed to mount with the multi-axis stage 100 and provide thermal heating or cooling functionality to the multi-axis stage 100. Top plate 650 can rotate around its axis driven via the base 601.

As can be envisioned, when a multi-axis stage is mounted into the mounting bracket 660, the stage can rotate in 360 degrees on top of the roller bearings (for example ball bearings or needle bearings) and still maintain thermal connectivity with the heat transfer medium that is flowing through the pipe 616. In this embodiment, all parts may be designed with a high thermal conductivity. For example, the roller bearings can be made of steel with a conductivity of 46 W/mK. The cold stage parts can be made of oxygen free copper, or other materials with a high thermal conductivity, for example, gold. In some embodiments, the temperature of the shuttle receiver can go down to −120° C., −130° C., −140° C., −150° C., −160° C., −170° C., −180° C. or less in temperature. In some embodiments, the device can be used to transfer heat such that the system is heated rather than cooled by pumping heated liquid or gas into the pipe 616.

It is noted that the stage can be equipped with one roller bearing offering the needed mechanical support and degree of freedom, while the stage further shows a second roller bearing thermally connecting the stage with a stationary cooling body, cooled by, for example, liquid nitrogen.

Detecting Frozen Status of Ice

Another embodiment relates to determining the status of vitreous ice in samples. This normally relies on TEM electron diffraction patterns usually taken at the thin sectioned area of interest on the frozen sample. Vitreous ice status is useful for to preserving natural structural forms, such as biological cell membranes or dispersed particulates. In contrast, crystalline ice disrupts those structures or distributions. Ring patterns show that the ice is amorphous (vitreous) whereas spot patterns show the presence of hexagonal or cubic crystalline structure. Quite often the vitreous result can be in dispute due to too sharp or too dull diffraction rings, or by which TEM electron gun it was produced; W, LaB6 or FEG.

When TEM sections are made one wants to know if the surrounding ice is crystalline or vitreous at that point. This helps the user know whether it is useful to continue with that sample or to start with a fresh sample.

One alternate embodiment is a method that can be used in the field emission gun SEM or SEM for samples where it is important to keep the temperature below the glass transition temperature of 136K (−137 deg C.). In this embodiment, the ice sample is FIB milled to the desired thickness so that when rotated and tilted to a horizontal plane it can be observed by an analyzing detector from below using the electron beam at a desired voltage. Tilting the ice sample from the horizontal plane to either a positive or negative angle allows the analyzing detector to observe a differing transmitted orientation contrast. This differing orientation contrast comes from the lattices of the differently orientated crystals within the thin sample if a crystalline form is present. If a crystalline form is not present because the sample is vitreous then the contrast remains constant as the sample is tilted.

This allows one to detect whether the sample has formed crystalline ice or not. The reason for this is that vitreous status is a state of random atomic structure and therefore will not show orientation contrast. This is a very direct and reliable way of determining the ice status of the sample when immediately made in a FEG SEM without having to make further transfer to a cryo-TEM system during which hexagonal ice contamination could compromise the result. With improvement of the SEM and Dual Beam instruments to resolve sub-nanometer resolution there are many cases where it is of little necessity to transfer to the TEM for direct resolution imaging or angular tomography. Therefore this method is convenient to verify the status of the sectioned ice within the SEM or Dual Beam instruments.

Equivalents

The foregoing written specification is considered to be sufficient to enable one skilled in the art to practice the present embodiments. The foregoing description and Examples detail certain preferred embodiments and describes the best mode contemplated by the inventors. It will be appreciated, however, that no matter how detailed the foregoing may appear in text, the present embodiments may be practiced in many ways and the present embodiments should be construed in accordance with the appended claims and any equivalents thereof.

The term "comprising" is intended herein to be open-ended, including not only the recited elements, but further encompassing any additional elements.

What is claimed is:

1. A multi-axis sample preparation stage, comprising:
   a bulk sample holder configured to rotate a sample position about a first bulk axis parallel to the direction of the bulk sample holder and also rotate the sample position about a bulk flip axis that is perpendicular to the direction of the bulk sample holder; and
   a grid sample holder for holding a sample grid adjacent the bulk sample holder and configured to rotate the sample grid about a first grid axis parallel to the direction of the grid sample holder and a grid flip axis that is perpendicular to the direction of the grid sample holder.

2. The multi-axis sample preparation stage of claim 1, further comprising a thermal control system in contact with the bulk sample holder and the grid sample holder.

3. The multi-axis sample preparation stage of claim 2, wherein the thermal control system comprises a series of rollers configured to allow the multi-axis sample preparation stage to rotate in 360 degrees or more.

4. The multi-axis sample preparation stage of claim 2, wherein the thermal control system is configured to reduce the temperature of the grid sample holder and bulk sample holder to −150° C. or more.

5. The multi-axis sample preparation stage of claim 1, wherein the bulk sample holder and grid sample holder is configured to hold at least one of a grid, planchet, or tube.

6. The multi-axis sample preparation stage of claim 1, wherein the bulk sample holder or the grid sample holder is configured to rotate 360 degrees.

7. The multi-axis sample preparation stage of claim 1, further comprising a detector for performing S/TEM microscopy.

8. A dual beam system having a focused ion beam column and a scanning electron microscope column, comprising the multi-axis sample preparation stage of claim 1.

9. The dual beam system of claim 8, further comprising a thermal control system in contact with the bulk sample holder and the grid sample holder.

10. The dual beam system of claim 9, wherein the thermal control system comprises a series of rollers configured to allow the multi-axis sample preparation stage to rotate in 360 degrees or more.

11. The dual beam system of claim 9, wherein the thermal control system is configured to reduce the temperature of the grid sample holder and bulk sample holder to −150° C. or more.

12. The dual beam system of claim 8, wherein the bulk sample holder and grid sample holder is configured to hold at least one of a grid, planchet, or tube.

13. The dual beam system of claim 8, wherein the bulk sample holder or the grid sample holder is configured to rotate 360 degrees.

14. An in situ method of preparing a sample, comprising:
   providing the multi-axis sample preparation stage of claim 1;
   cutting a lamella from a sample stored in the bulk sample holder; and
   transferring the lamella from the bulk sample holder to a grid on the grid sample holder.

15. The method of claim 14, wherein cutting a lamella comprises using a focused ion beam to cut a lamella from the region of interest of a bulk sample.

16. The method of claim 14, wherein a manipulator is attached to the lamella by soldering a tip of the manipulator to the lamella.

17. The method of claim 14, further comprising imaging the lamella.

18. The method of claim 14, further comprising rotating the lamella to determine if the lamella comprises vitreous or crystalline ice.

* * * * *